US012576270B2

(12) United States Patent
Gruba et al.

(10) Patent No.: US 12,576,270 B2
(45) Date of Patent: Mar. 17, 2026

(54) MEDICAL DEVICES FOR ELECTROPORATION

(71) Applicant: Boston Scientific Scimed, Inc., Maple Grove, MN (US)

(72) Inventors: Sarah Melissa Gruba, Vadnais Heights, MN (US); Troy Anthony Giese, Blaine, MN (US); James A. Klos, Bay City, WI (US); James P. Rohl, Prescott, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1288 days.

(21) Appl. No.: 17/218,221

(22) Filed: Mar. 31, 2021

(65) Prior Publication Data

US 2021/0308450 A1      Oct. 7, 2021

Related U.S. Application Data

(60) Provisional application No. 63/005,588, filed on Apr. 6, 2020.

(51) Int. Cl.
*A61M 25/10*          (2013.01)
*A61B 18/14*          (2006.01)
          (Continued)

(52) U.S. Cl.
CPC .......... *A61N 1/327* (2013.01); *A61B 18/1492* (2013.01); *A61B 2018/00238* (2013.01);
          (Continued)

(58) Field of Classification Search
CPC ...... A61B 18/1492; A61B 2018/00214; A61B 5/287; A61B 2017/00243;
          (Continued)

(56) References Cited

U.S. PATENT DOCUMENTS 5,507,724 A * 4/1996 Hofmann ............... A61N 1/306
                                                              607/116
6,148,222 A    11/2000 Ramsey, III
          (Continued)

FOREIGN PATENT DOCUMENTS

CN          110313987 A      10/2019
CN          110693607 A      1/2020

OTHER PUBLICATIONS

International Search Report an Written Opinion issued in International Application PCT/US2021/025023, mailed on Jul. 6, 2021 (11 pages).

*Primary Examiner* — Joseph A Stoklosa
*Assistant Examiner* — Brian M Antiskay
(74) *Attorney, Agent, or Firm* — Bookoff McAndrews, PLLC

(57) ABSTRACT

A medical device comprising a tube, a first electrode and a second electrode, and a structure at a distal portion of the tube, the structure defining a first section and a second section, wherein the first and second sections are configured to be filled with a conductive medium, wherein the first electrode is contained within the first section, and the second electrode is contained within the second section, and wherein the structure includes a central barrier separating the first section from the second section, and the central barrier is insulative.

10 Claims, 7 Drawing Sheets

(51) Int. Cl.
  *A61N 1/32*     (2006.01)
  *A61B 18/00*    (2006.01)
  *A61N 1/05*     (2006.01)

(52) U.S. Cl.
  CPC ............... *A61B 2018/00488* (2013.01); *A61B 2018/00613* (2013.01); *A61B 2018/1467* (2013.01); *A61N 1/0517* (2013.01)

(58) Field of Classification Search
  CPC .. A61B 2018/0022; A61B 2018/00351; A61B 5/6853; A61B 2017/003; A61B 2018/00285; A61B 8/445; A61B 5/6852; A61B 1/00082; A61B 17/12136; A61B 2562/0217; A61N 1/05; A61M 25/10; A61M 2025/105; A61M 25/1011; A61M 2025/1052; A61M 25/0147; A61M 25/1002; A61M 25/0041; A61M 2025/1086; A61M 2025/0057; A61M 2210/125; A61M 2025/0681; A61M 31/002; A61M 16/0481; A61M 31/00; A61M 25/0043; A61M 5/00; A61M 2025/1072; A61M 2025/1015; A61M 25/1027; A61M 25/0026; A61M 2025/1047; A61M 39/0208; A61M 25/1006; A61M 2025/1065; A61M 60/843
  USPC ........ 600/115–116, 372–375, 377, 380–381, 600/393, 433–435, 466, 470; 604/93.01, 604/95.03, 96.01, 101.01, 101.02, 101.03, 604/101.04, 101.05, 102.01, 103.01, 604/103.02, 103.03, 103.04, 103.5; 606/32; 607/115–116, 119–123
See application file for complete search history.

(56)        References Cited

U.S. PATENT DOCUMENTS

| | | | |
|---|---|---|---|
| 6,685,672 B1 * | 2/2004 | Forman .............. | A61M 25/1011 604/101.03 |
| 6,776,771 B2 * | 8/2004 | van Moorlegem . | A61M 25/104 604/103.02 |
| 6,917,834 B2 * | 7/2005 | Koblish ............. | A61B 18/1492 606/41 |
| 7,658,744 B2 * | 2/2010 | Jackson ......... | A61B 17/320725 606/159 |
| 8,034,022 B2 * | 10/2011 | Boatman ............. | A61M 25/104 604/101.02 |
| 2003/0045869 A1 * | 3/2003 | Ryan ...................... | A61B 18/04 606/41 |
| 2007/0083192 A1 | 4/2007 | Welch | |
| 2009/0259274 A1 | 10/2009 | Simon et al. | |
| 2011/0275980 A1 * | 11/2011 | Weber .................... | A61L 29/14 604/20 |
| 2013/0030353 A1 * | 1/2013 | Seymour ............. | A61N 5/0622 604/20 |
| 2013/0030410 A1 * | 1/2013 | Drasler .................. | A61B 18/04 604/510 |
| 2013/0190796 A1 | 7/2013 | Tilson et al. | |
| 2016/0228182 A1 * | 8/2016 | Levin .............. | A61M 25/10185 |
| 2017/0035498 A1 * | 2/2017 | Boden ............... | A61B 18/1492 |
| 2017/0354463 A1 * | 12/2017 | Mori .................. | A61B 18/1492 |
| 2018/0296264 A1 | 10/2018 | DeSimone et al. | |
| 2018/0311497 A1 | 11/2018 | Viswanathan et al. | |
| 2019/0133528 A1 * | 5/2019 | Kassab ................. | A61F 2/2496 |
| 2020/0316350 A1 * | 10/2020 | Patel ...................... | A61N 1/325 |

* cited by examiner

MEDICAL DEVICES FOR ELECTROPORATION

CROSS-REFERENCE TO RELATED APPLICATIONS

This application claims the benefit of priority from U.S. Provisional Application No. 63/005,588, filed on Apr. 6, 2020, which is incorporated by reference herein in its entirety.

TECHNICAL FIELD

This disclosure relates generally to medical devices for electroporation. Examples of the disclosure relate to devices for tissue ablation via irreversible electroporation, and drug delivery via reversible electroporation.

BACKGROUND

Barrett's esophagus is a disease state in which the esophageal lining next to the stomach is replaced by tissue similar to the intestinal lining. Individuals with Barret's esophagus are at a higher risk of developing esophageal cancer. If cancer cells are found, treatment may typically entail relatively invasive surgery, e.g., esophagectomy, esophagogastrostomy, photodynamic therapy, chemotherapy, and/or radiation. Treatment may also include therapies involving high heat to kill the cancer cells. Such heat treatments may cause incidental burning and/or scarring of the esophagus.

SUMMARY OF THE DISCLOSURE

According to an example, a medical device may comprise a tube, a first electrode and a second electrode, and a structure at a distal portion of the tube, the structure defining a first section and a second section, wherein the first and second sections are configured to be filled with a conductive medium, wherein the first electrode is contained within the first section, and the second electrode is contained within the second section, and wherein the structure includes a central barrier separating the first section from the second section, and the central barrier is insulative.

In another example, the structure may further include a proximal barrier and a distal barrier, wherein a space between the distal barrier and the central barrier defines the first section, and a space between the proximal barrier and the central barrier defines the second section, and wherein the proximal barrier and the distal barrier are insulative. The proximal barrier, the central barrier, and the distal barrier may be balloons configured to be inflated. The first section and/or the second section may be filled with a porous material, wherein the porous material provides an electrical pathway.

In another example, the first section may be covered by a first membrane, and the second section may be covered by a second membrane, wherein the first membrane and the second membrane are porous. The structure may include a first balloon and a second balloon separated by a distance, a cavity of the first balloon defining the first section and a cavity of the second balloon defining the second section, wherein the first balloon and the second balloon comprise porous membranes, and wherein the central barrier comprises a proximal coating on a proximal portion of the first balloon and a distal coating on a distal portion of the second balloon, wherein the proximal coating of the first balloon and the distal coating of the second balloon insulate and seal the coated porous membranes. The first balloon may further comprises a distal coating on a distal portion of the first balloon and the second balloon further comprises a proximal coating on a proximal portion of the second balloon, and the distal coating of the first balloon and the proximal coating of the second balloon insulate and seal the coated porous membranes, wherein a portion of the porous membrane between the distal coating and the proximal coating of the first balloon defines a first porous portion, and a portion of the porous membrane between the distal coating and the proximal coating of the second balloon defines a second porous portion.

According to another example, the structure may include a balloon comprising a distal endcap, a proximal endcap, and a porous membrane between the distal endcap and the proximal endcap, wherein the distal endcap and the proximal endcap are insulative and non-porous, wherein a cavity of the balloon is divided by the central barrier, thereby forming a first cavity and a second cavity that are adjacent, and wherein the first cavity defines the first section and the second cavity defines the second section. The central barrier may include a nonporous membrane extending along a circumference of the central barrier, and wherein a portion of the porous membrane between the distal endcap and the nonporous membrane of the first balloon may define a first porous portion, and a portion of the porous membrane between the proximal endcap and the nonporous membrane of the second balloon defines a second porous portion.

In another example, the structure may include an inner balloon and an outer balloon housing the inner balloon, wherein the outer balloon comprises a porous membrane, and the inner balloon is insulative, wherein the central barrier comprises the inner balloon and an insulative seal between an inner wall of the outer balloon and the inner balloon, thereby dividing a cavity of the outer balloon into a first cavity and a second cavity, wherein the first cavity defines the first section and the second cavity defines the second section, and wherein the outer balloon comprises a central coating around a central portion of the porous membrane, wherein the central coating insulates and seals the coated porous membrane. The outer balloon may further comprise a coating around a distal portion and a proximal portion of the outer balloon, and the distal coating and the proximal coating of the outer balloon insulate and seal the coated porous membranes, wherein a portion of the porous membrane between the distal coating and the central coating of the outer balloon defines a first porous portion, and a portion of the porous membrane between the central coating and the proximal coating of the outer balloon defines a second porous portion. The proximal coating, the central coating, and the distal coating of the outer balloon may include silicone.

In another example, the conductive medium is a fluid. The conductive medium of the first section may be oppositely charged from the conductive medium of the second section, or the conductive medium of the first section may be of a different voltage potential than the conductive medium of the second section. A proximal end of the tube may be connected to an electrical source, and the tube may be configured to supply a current from the electrical source to the first electrode and the second electrode.

According to another example, a medical device may comprise a tube including a distal end having a conductive tip, at least one electrode, and an expandable structure at a portion of the tube proximal to the distal end, the structure defining a cavity configured to be filled with a conductive medium, wherein the at least one electrode is contained within the cavity, and wherein the structure includes an insulated and nonporous distal portion and an insulated and nonporous proximal portion, thereby defining a porous portion between the distal portion and the proximal portion. The at least a distal portion of the tube may be configured to be steerable. The expandable structure may be a balloon fixed to the portion of the tube. The conductive medium may be a fluid.

According to an example, a method of electroporation via a medical device, the medical device including a tube, and a structure at a distal portion of the tube, the structure defining a first section containing a first electrode and a second section containing a second electrode, the method may include positioning the medical device within a body lumen, filling the first section and the second section with a conductive medium, and providing an electrical current to the first electrode and the second electrode via a conductor in the tube.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Figure 1A:
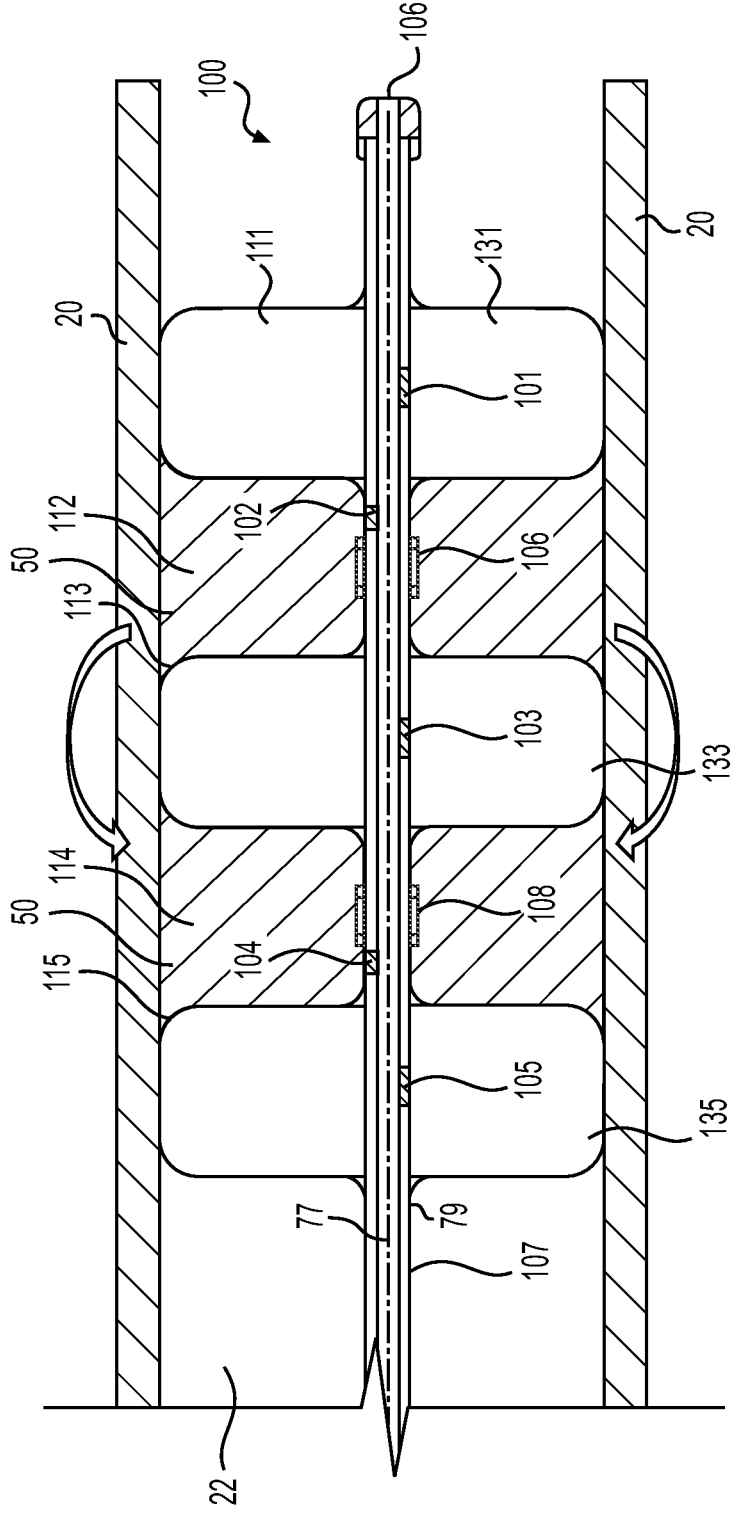
FIG. 1A is a cross-sectional view of a medical device for electroporation, according to some aspects of the disclosure.

Reference will now be made in detail to aspects of the disclosure, examples of which are illustrated in the accompanying drawings. Wherever possible, the same or similar reference numbers will be used through the drawings to refer to the same or like parts. The term "distal" refers to a location or portion of a medical device farthest away from a user of the device, e.g., when introducing a device into a subject (e.g., patient). By contrast, the term "proximal" refers to a location or portion closest to the user, e.g., when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of this disclosure include medical devices, systems, and methods for treating tissue of a body lumen, e.g., esophageal tissue, via electroporation. Electroporation, e.g., a high pulsed electric field, involves creating an electric field between two or more electrodes, and sending high voltage, short pulses to nearby tissue. This may cause cell pores of the tissue to open up, thereby disrupting homoeostasis. Depending on the pore size, the cell may recover, e.g., reversible electroporation, or not recover, e.g., irreversible electroporation. The strength of the electric field may determine whether reversible or irreversible electroporation takes places. For example, an electric field having a voltage of 0-600 V/cm may trigger reversible electroporation, whereas an electric field having a voltage at least 600 V/cm, or 600-3,000 V/cm, may trigger irreversible electroporation. Reversible electroporation may open the pores of cells. Irreversible electroporation may cause cells to go through apoptotic cell deaths, without causing a large immune response and/or scarring of the tissue. Thus, during treatment, reversible electroporation may provide optimal drug delivery by opening up cell pores, and irreversible electroporation may provide controlled ablation of the tissue between the electrodes of the generated electric field. Irreversible electroporation may also result in reversible electroporation at the edges of the targeted tissue. Thus, irreversible electroporation may allow for both ablation of nearby tissue and optimal drug delivery to edges of the ablated tissue. Furthermore, because ablation is via irreversible electroporation, burns or other detrimental effects typically associated with thermal treatments are minimized. It is noted, however, that irreversible electroporation, at voltages significantly greater than 3,000 V/cm, e.g., 10,000 V/cm, may cause nerve ablation.

Exemplary medical devices of this disclosure may include electrodes surrounded by an energy-delivering medium. The electrodes are not particularly limited, and may be of any suitable material, e.g., steel, nitinol, etc., and form, e.g., a ring, wire, tubes, prongs, coils etc. The energy-delivering medium is in contact with or adjacent to the targeted tissue, thereby allowing the generated electric field to travel from the electrode to the adjacent tissue. A medium may eliminate the need for an electrode to contact, or be located near the tissue surface. Furthermore, a first electrode (or a group of electrodes) may be charged opposite from an adjacent second electrode (or group of electrodes). A first medium for that first electrode (or group of electrodes) may therefore be charged oppositely from a second medium of the second electrode (or group of electrodes), and be isolated from that second medium, thereby causing an electric field to travel from the first medium to the second medium. Such a medium is not particularly limited, and may be, for example, any suitable conductive fluid, e.g., 0.9% saline. A medium such as conductive fluid may help dissipate heat generated from the electrodes.

Furthermore, exemplary devices of this disclosure may also include insulative structures. The type of insulative structures is not particularly limited, and may be any suitable structure, such as, balloons, discs, non-porous foams, molded silicone components, etc. Insulative structures may serve as a barrier or a seal between oppositely-charged electrodes and their respective mediums. In some exemplary embodiments, insulating coatings may be applied to structures to form insulative portions, in place of insulative structures. Thus, sections/cavities containing an electrode and a medium, e.g., conductive fluid, may be sealed by insulative structures/portions and surrounding tissue of a body lumen. Because the electric field travels from an oppositely charged medium to the other, such a configuration forces the electric field generated via the electrodes to pass through the adjacent tissue and around the insulative structure/portion. Thus, this may result in ablation of the tissue, from one section containing an electrode and medium to another section containing the same. It is noted that the distance between sections is not particularly limited. However, distance between said sections may determine the amount of electrical energy necessary to generate an electric field (V/cm) sufficient for reversible electroporation or irreversible electroporation, e.g., ablation.

Referring to FIG. 1A, an exemplary medical device 100, surrounded by tissue 20 defining a body lumen 22, is shown. Medical device 100 includes a tube 107, insulative structures 111, 113, 115, and electrodes 106, 108. Tube 107 is not particularly limited and may be any suitable biocompatible tubing, e.g., a catheter. Tube 107 may include a proximal end (not shown) and a distal end 106. The proximal end may be connected to any suitable supply source(s), e.g., an electrical supply and/or a fluid supply, and/or a controller (not shown). The controller may be any suitable controller for controlling the movement of device 100 and/or the supply of energy or fluid from sources. Distal end 106 is not particularly limited, and may include openings for any suitable accessory devices, such as a guidewire, an imaging system, a lighting system, biopsy tools, etc. Tube 107 may further include a tubing wall 79 and a lumen 77, through which any wirings and/or accessory devices may extend, and/or fluids may be supplied. Furthermore, there may be multiple discrete lumens for various different functions, e.g., balloon inflation, drug delivery, guidewire, electrical wires, etc. Tube 107 may further include a plurality of outlets 101, 102, 103, 104, 105 through which any suitable fluid, e.g., air, water, saline, etc., may be dispensed.

In examples, insulative structures 111, 113, 115 are inflatable balloons, but are not limited thereto. Balloons 111, 113, 115 may be of any suitable insulative, non-porous material, e.g., urethane, silicone. Balloons 111, 113, 115 may be compliant or noncompliant. Balloons 111, 113, 115 may be coupled to a distal portion of tube 107, so that each of the balloons is fixed around an outer circumference of tube 107. The distance between each of balloons 111, 113, 115 is not particularly limited. Balloons 111, 113, 115 may be fixed over outlets 101, 103, and 105 of tube 107, so that the balloons may be inflated with fluid, e.g., air, saline, or water, dispensed via the outlets. Thus, inflated balloons 111, 113, 115 may expand/jut radially outward, relative to tube 107, so that they abut surrounding tissue 20.

As shown in FIG. 1A, inflated balloons 111, 113, 115, along with surrounding tissue 20, may seal off and form cavities/sections 112 and 114. Sections 112 and 114 may respectively contain portions of tube 107, which electrodes 106 and 108 are fixed onto. In examples, electrodes 106 and 108 are metal rings fixedly surrounding tube 107. However, as discussed above, electrodes 106 and 108 are not particularly limited, and may be of any suitable material, e.g., steel, nitinol, etc., and any suitable form, e.g., a ring(s), wire(s), tube(s), prong(s), etc. Electrodes 106 and 108 may be connected to an electrical supply via any suitable manner. For example, wirings (not shown) running through lumen 77 of tube 107 may connect electrodes 106 and 108 to a generator at a proximal end of tube 107. Thus, electrodes 106 and 108 may be supplied with energy at any desired time, via control of said electrical supply, e.g., generator. Sections 112 and 114 may respectively contain outlets 102 and 104 of tube 107, which may dispense a conductive fluid 50, e.g., 0.9% saline and saline contrast mixture. Sections 112 and 114 may be filled with conductive fluid 50 until fluid 50 is in contact with or adjacent to tissue 20. Furthermore, conductive fluid 50 in section 112 may be oppositely charged from conductive fluid of section 114, as described above, so that oppositely charged mediums are contained in sections 112 and 114. Thus, an electric field generated by electrodes 106 and 108 is forced to pass through adjacent tissue 20 and around insulative structure 113, to travel from section 112 to section 114 and vice versa.

Device 100 (and subsequent exemplary devices further discussed below) may also be utilized for drug delivery. In some examples, outlets 102 and 104 may dispense drugs or agents, e.g., cytotoxic agents, along with or independent of conductive fluid 50. In other examples, drugs or agents may be adhered externally onto balloons 111, 113, 115 and be pushed up against surrounding tissue 20. Regardless of the method of delivery, the delivered drugs or agents may be effectively absorbed during reversible electroporation, which opens up cell pores and allows easier migration of the drugs/agents into the cell.

In view of the above, device 100 may include a delivery configuration and a treatment configuration. In the delivery configuration, balloons 111, 113, 115 may be in a deflated, contracted state, thereby allowing device 100 to more easily traverse body lumen 22. In a treatment configuration, which is shown in FIG. 1A, balloons 111, 113, 115 may be inflated (expanded) to create sealed sections 112 and 114, and sections 112 and 114 may be filled with conductive fluid 50.

Referring to FIG. 1A, an example of how medical device 100 may be delivered and used is further discussed below. A user may deliver device 100, while in its delivery configuration, into the body of a subject, e.g., via a natural orifice (such as a mouth). Device 100 may traverse through a tortuous natural body lumen 22 of the subject, such as an esophagus, stomach, colon, etc. Device 100, via tube 107, may be delivered in any suitable way, for example, through a working channel of an endoscope, or by itself. Alternatively, device 100 and tube 107 may be placed in a patient via a nasogastric tube. A user may direct/position device 100 within the body lumen 22 adjacent the targeted tissue 20, for electroporation treatment. A user may then transition device 100 to a treatment configuration by inflating balloons 111, 113, 115, via outlets 101, 103, 105, until balloons 111, 113, 115 contact tissue 20, to form sealed sections 112 and 114. Subsequently, a user may fill sections 112 and 114 with conductive fluid 50, e.g., 0.9% saline, via outlets 102 and 104, until conductive fluid 50 is in contact with or adjacent to tissue 20. A user may then turn on the electricity source at any suitable time to supply a voltage differential between the two electrodes 106 and 108, via electrical wirings (not shown) extending through lumen 77 of tube 107. The changes applied to electrodes 106, 108 may be opposite from one another, resulting in conductive fluid 50 in section 112 being oppositely charged from conductive fluid 50 in section 114. Alternatively, one of electrode 106, 108 may be charged, e.g., positively, while the other electrode 106, 108 is neutral/ground, with fluid 50 in sections 112 and 114 reflecting the same.

Figure 1B:
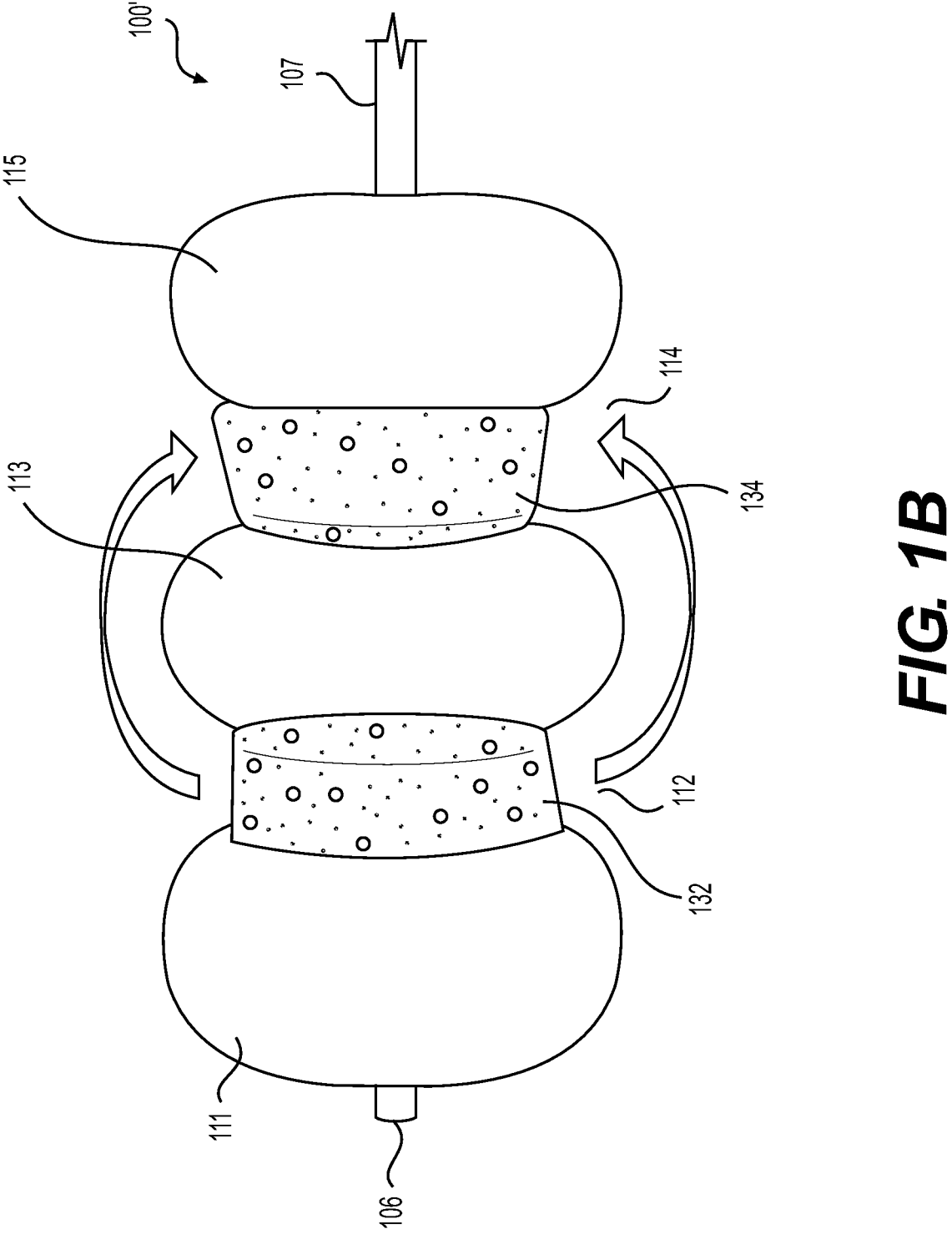
FIG. 1B is a perspective view of another exemplary medical device for electroporation, according to some aspects of the disclosure.

Medical device 100', as shown in FIG. 1B, is similar to device 100 in many respects. Like reference numerals refer to like parts. Differences between device 100 and device 100' will be described below. Device 100' further includes porous materials in between balloons 111, 113, 115, e.g., sponge 132 in section 112 and a sponge 134 in section 114. Sponges 132 and 134 are fixed to, and surround, the portion of tube 107 contained within sections 112 and 114. Sponges 132 and 134 may, respectively, partially or fully fill sections 112 and 114. The porous materials, however, are not limited to being a sponge, and may be any suitable porous material as long as there is an electrical pathway between the electrodes (106 and 108 shown in FIG. 1A) and surrounding tissue (20 shown in FIG. 1A). Sponges 132 and 134, among other benefits, may assist in preventing balloons 111, 113, 115 from contacting and folding over one another. Device 100' may be used in a similar manner as device 100.

Figure 1C:
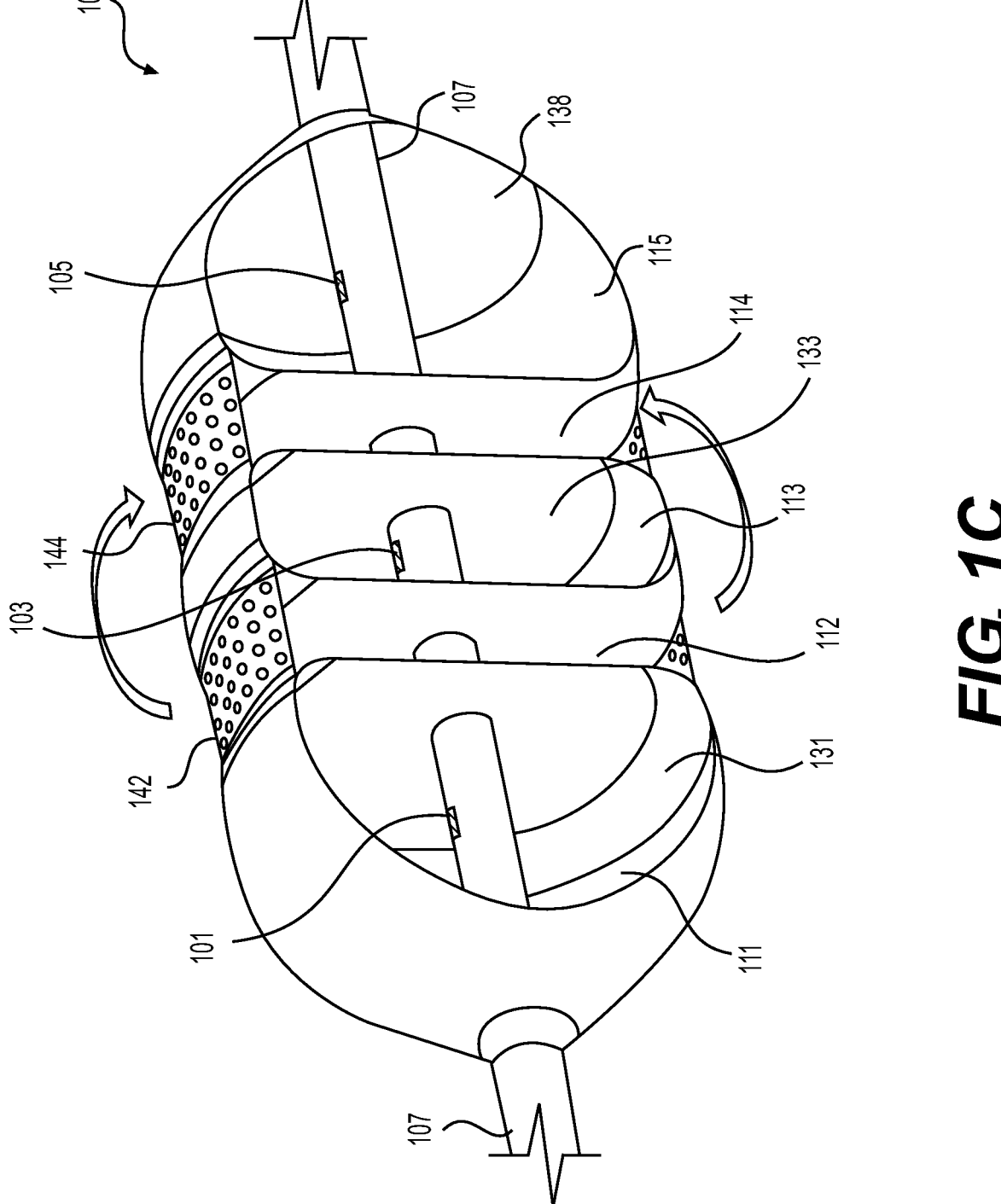
FIG. 1C is a sectional view of another exemplary medical device for electroporation, according to some aspects of the disclosure.

Medical device 100", as shown in FIG. 1C, is similar to device 100 in many respects. Like reference numerals refer to like parts. Differences between device 100 and device 100" will be described below. Device 100" further includes perforated barriers 142 and 144 respectively surrounding sections 112 and 114. The manner by which perforated barriers 142 and 144 are formed is not particularly limited. In some exemplary embodiments, barriers 142 and 144 may be perforated strips which are adhered to the outer surfaces of balloons 111, 113, 115. In other exemplary embodiments, barriers 142 and 144 may be perforated portions of a surface of a single balloon containing a plurality of inner compartments or balloons (111, 112, 113, 114, and 115). Barriers 142 and 144 may also help limit balloons 111, 113, 115 from contacting and folding over one another, while also providing an electrical pathway between electrodes (106 and 108 shown in FIG. 1) and surrounding tissue (20 shown in FIG. 1). Furthermore, barriers 142 and 144 allow for a controlled distance between sections 112 and 114, and also ensure contact with the surrounding tissue. Device 100" may also be used in a similar manner as device 100.

Figure 2A:
FIG. 2A is a transparent view of another exemplary medical device for electroporation, according to some aspects of the disclosure.

Medical device 400, as shown in FIG. 2A, is similar to device 100 in many respects. Like reference numerals refer to like parts. Differences between device 100 and device 400 will be described below. Device 400 includes electro-spun balloons 431 and 433, spaced apart from one another by a distance D. Distance D is not particularly limited. Balloons 431 and 433 may both be electro-spun on a distal portion of tube 107. The manner by which balloons 431 and 433 are electro-spun onto tube 107 is not particularly limited. In some examples, balloons 431 and 433 may be electro-spun over an ice mold that is initially formed on tube 107. Electro-spun balloons 431 and 433 respectively house electrode wires 406 and 408, extending from tube 107, and leading to electrodes 406', 408'. Balloon 431 houses four electrode wires 406, each leading to an electrode 406' (four electrodes 406' in total). Likewise, balloon 433 houses four electrode wires 408, each leading to an electrode 408' (four electrodes 408' in total). Electrode wires 406 and 408 extend from tube 107. Electrode wires 406 extend radially outward and proximally from a distal end of the portion of the tube 107 housed by balloon 431. Electrode wires 408 extend radially outward and distally from a proximal end of the portion of the tube 107 housed by balloon 433. However, it is noted that the number of electrode wires and electrodes, the pattern of said wires and electrodes, and their positions within balloons 431 and 433 is not particularly limited. Like in the previously described embodiments, electrodes 406' and 408' may be a connected to an electrical supply, e.g., a generator, via wirings (not shown) running through a lumen ('77' shown in FIG. 1A) of tube 107.

Balloons 431 and 433 are inflated with an energy-delivering medium, e.g., conductive fluid 50, which may be dispensed via outlets (not shown in FIG. 2A) along tube 107.

Balloons 431 and 433 may be of any suitable electro-spun polymer fibers, e.g., chronoflex. Due to the walls/membranes of balloons 431 and 433 being of electro-spun fibrous mesh, balloons 431 and 433 may be porous by default. As a result, conductive fluid 50 may be in contact with the surrounding tissue, when inflated balloons 431 and 433 abut said tissue. Because the membranes of balloons 431 and 433 are porous by default, distal and proximal portions of the membranes of balloons 431 and 433 may be coated with an insulating material, e.g., silicone. For example, as shown in device 400, insulated distal portion 411 and proximal portion 413 of balloon 431, and insulated distal portion 415 and proximal portion 417 of balloon 433 may include a silicone outer coating. Insulated portions 413 and 415 may serve as insulative barriers between conductive fluid 50 of balloons 431 and 433. As a result of defining said insulated portions, circumferential porous strip 412 around balloon 431 and circumferential porous strip 414 around balloon 433 may likewise be defined. In view of the above configuration, an electric field generated by electrodes 406 and 408 is forced to pass through porous strip 412, through adjacent tissue due to insulative portions 411 and 413, and through porous strip 414, to travel from balloon 431 to balloon 433 and vice versa. Thus, electroporation (reversible or irreversible) may take place between tissue adjacent to porous strip 412 and tissue adjacent to porous strip 414. However, it is noted that in some embodiments (including those discussed in further detail below), select portions of the porous strip(s), e.g., 412 and 414, may also be coated with insulating material. This may be done to direct the electric field towards a more specific location/area of the surrounding tissue.

Device 400 may be used in a similar manner as device 100 except a user may transition device 400 to a treatment configuration by inflating balloons 431 and 433 with conductive fluid 50, e.g., 0.9% saline. Balloons 431 and 433 may be inflated until the balloons abut the surrounding tissue. Conductive fluid 50 may be dispensed via outlets (not shown) on the portions of tube 107 encapsulated by balloons 431 and 433.

Figure 2B:
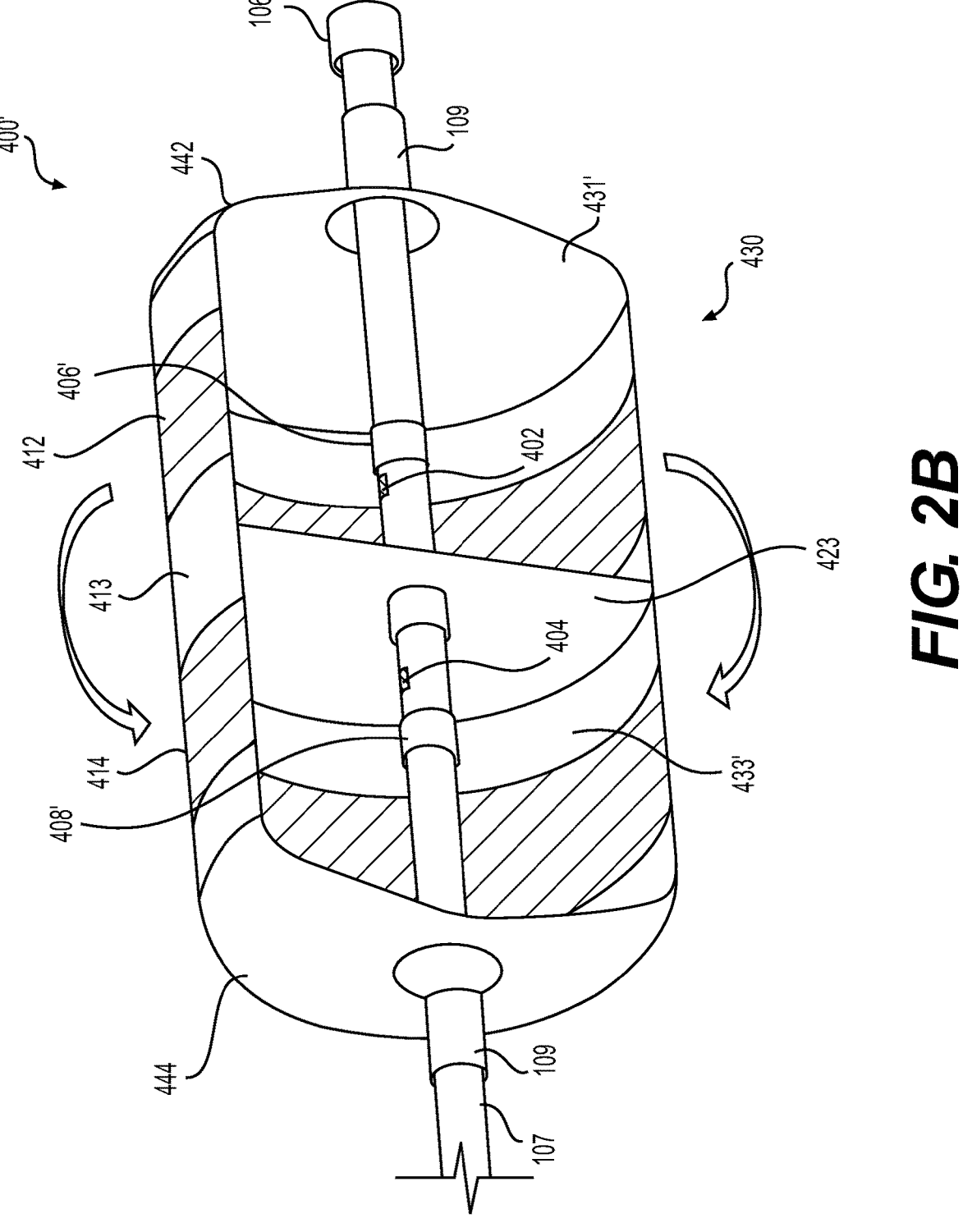
FIG. 2B is a sectional view of another exemplary medical device for electroporation, according to some aspects of the disclosure.

Medical device 400', as shown in FIG. 2B, is similar to device 400 in many respects. Like reference numerals refer to like parts. Differences between device 400 and device 400' will be described below. Unlike device 400, which includes electro-spun balloons 431, 433 separated by a distance D, device 400' includes a single balloon 430. Balloon 430 may include insulative endcaps 442 and 444, which define the proximal and distal ends of balloon 430. Endcaps 442 and 444 may be fixed around mandrels 109 of tube 107. Endcaps 442 and 444 may be of any suitable insulating material, e.g., silicone. In addition, device 400' may include a central barrier 423 that is fixed within balloon 430. Central barrier 423 may include a central membrane 413 extending along the circumference of central barrier 423. Central membrane 413 may be a non-porous, insulative membrane. Central membrane 413 may jut outwards relative to barrier 423, so that membrane 413 extends along a portion of the longitudinal axis of tube 107, on both sides of central barrier 423. A membrane may be electro-spun between endcap 442, central membrane 413, and endcap 444 to form the remaining walls of balloon 430. The manner by which this is done is not particularly limited. In some examples, central membrane 413 and two end rings (not shown), defining surfaces onto which endcaps 442 and 444 may be fixed, may be placed on a mandrel. Afterwards, a liquid adhesive, e.g., silicone, may be applied on the outer surfaces of membrane 413 and the two end rings. Electro-spinning may then be applied between the end rings, and additional adhesives, e.g., silicone, may then be applied over pre-formed parts, e.g., membrane 13. Said mandrel may then be removed and endcaps 442 and 444 may be bonded to the end rings using an insulative adhesive, e.g., silicone. Thus, as a result of central membrane 413, circumferential porous strip 412 between distal endcap 442 and central membrane 413 413, and circumferential porous strip 414 between proximal endcap 444 and central membrane 413 may be defined. However, it is noted that the manner of electro-spinning is not limited to the above description, as any suitable manner of electro-spinning may be used.

Central barrier 423 forms two adjacent cavities 431', 433' within balloon 430. Barrier 423 may be fixed to tube 107 via any suitable manner, e.g., silicone, medical adhesive, etc., to seal cavities 431', 433' from one another. Barrier 423 may be of any suitable insulative material, e.g., silicone.

Cavities 431' and 433' may house electrodes rings 406' and 408', which are fixed to tube 107. Thus, an electric field generated by electrodes 406' and 408' is forced to pass through porous strip 412, through adjacent tissue to get around central barrier 423 and central membrane 413, and through porous strip 414, to travel from cavity 431' to cavity 433' and vice versa. Thus, electroporation (reversible or irreversible) may take place between tissue adjacent to porous strip 412 and tissue adjacent to porous strip 414. It is further noted that an electric field (V/cm) generated by device 400' may require less voltage than that of device 400. This is because porous strips 412 and 414 of device 400' may be closer in proximity than those of device 400. For example, the distance between porous strips 412 and 414 in device 400 may be about 2-5 cm, while the distance between porous strips 412 and 414 in device 400' may be about 0.5 cm or greater.

Device 400' may be used in a similar manner as device 400 except cavities 431' and 433' are filled with conductive fluid, e.g., 0.9% saline. Cavities 431' and 433' are filled with conductive fluid until porous strips 412 and 414 abut the surrounding tissue.

Figure 2C:
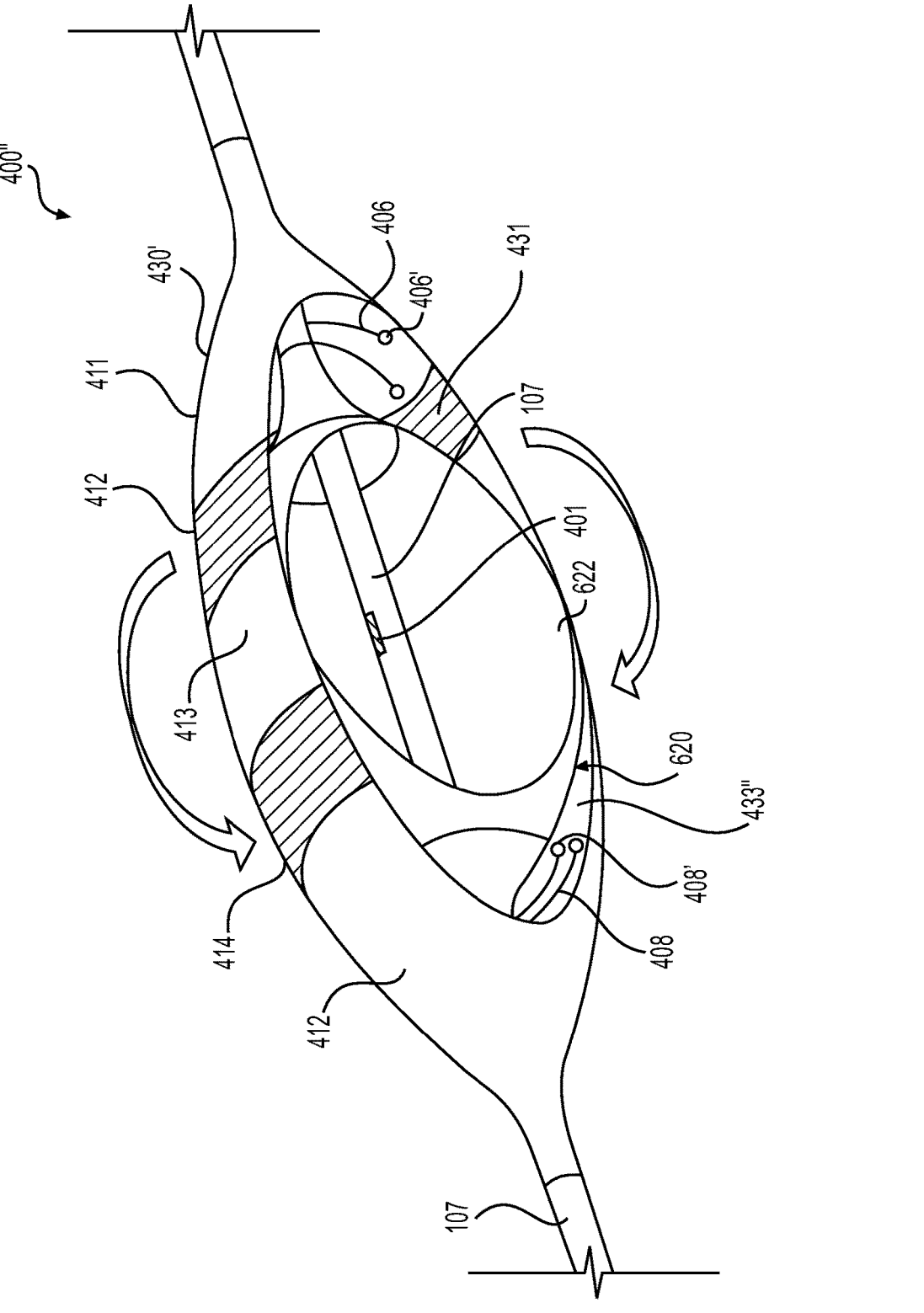
FIG. 2C is a sectional view of another exemplary medical device for electroporation, according to some aspects of the disclosure.

Medical device 400", as shown in FIG. 2C, is similar to device 400 in many respects. Like reference numerals refer to like parts. Differences between device 400 and device 400" will be described below. Device 400" includes an electro-spun inner balloon 620 and an electro-spun outer balloon 430'. Inner balloon 620 may be electro-spun and fixed around a distal portion of tube 107. The manner by which balloon 620 is electro-spun onto tube 107 is not particularly limited. The manner by which balloon 620 is fixed onto tube 107 is not particularly limited as well, and may be by any suitable means, e.g., adhesive, heat bonding, etc. Balloon 620 houses a portion of tube 107 including an outlet 401. Thus, cavity 622 of balloon 620 may be filled with any suitable fluid, e.g., air, saline, etc., dispensed via outlet 401, thereby inflating balloon 620. Balloon 620 is entirely coated with an insulative material, e.g., silicone, medical adhesive, etc., so that it may be insulated through-out. Electrode wires 406, 408 extending out of tube 107 may extend over proximal and distal portions of balloon 620. Electrode wire 406, 408 may be free to move radially outwards, in a direction towards the adjacent tissue, as inner balloon 620 is inflated, and pushes radially outward on wires 406, 408 and electrodes 406', 408'. Outer balloon 430' may also be electro-spun onto tube 107, so that it encapsulates inner balloon 620 and wires 406, 408 and electrodes 406', 408'. Cavity 431" houses two electrode wires 406, each leading to an electrode 406' (two electrodes 406' in total). Likewise, cavity 433" houses two electrode wires 408, each leading to an electrode 408' (two electrodes 408' in total).

Electrode wires 406 and 408 extend from tube 107. Electrode wires 406 extend radially outward and proximally from a distal end of the portion of the tube 107 housed by cavity 431". Electrode wires 408 extend radially outward and distally from a proximal end of the portion of the tube 107 housed by cavity 433". However, it is noted that the number of electrode wires and electrodes, the pattern of said wires and electrodes, and their positions within cavities 431" and 433" is not particularly limited. Again, the manner by which balloon 430' is electro-spun over inner balloon 620 is not particularly limited, and in some examples, may be via the use of an ice mold. The manner by which balloon 430' is fixed onto tube 107 is not particularly limited as well, and may be by any suitable means, e.g., adhesive, heat bonding, etc.

A central, circumferential portion of outer balloon 430' may be coated with an insulating material, e.g., silicone, medical adhesive, etc., thereby defining an insulated portion 413. Furthermore, proximal and distal portions of outer balloon 430' may also be coated with an insulating material, thereby defining a distal insulation portion 411 and a proximal insulated portion 415. By defining insulated portions 411, 413, 415, porous strip 412 between insulated portions 411 and 413, and porous strip 414 between insulated portions 413 and 415 may likewise be defined. Furthermore, a central portion of outer balloon 430' at portion 413 may be sealed to inner balloon 620 with an insulating material (e.g., silicone or a medical adhesive), thereby forming an inner barrier (not shown in FIG. 2C) that extends between the inner wall of outer balloon 430' and the surface of inner balloon 620. Thus, outer balloon 430' and the outer surface of inner balloon 620 may define adjacent cavities 431" and 433", which are separated by said barrier. Distal cavity 431" may house electrode wires 406 and electrode 406', and at least one outlet (not shown) configured to dispense a con-ductive fluid, thereby filling distal cavity 431". Similarly, proximal cavity 433" may house electrode wires 408 and electrode 408, and at least one outlet (not shown) configured to dispense a conductive fluid, thereby filling proximal cavity 433". Distal cavity 431" is at least partially defined by porous strip 412 and proximal cavity 433" is at least partially defined by porous strip 414.

Thus, in device 400", an electric field generated by electrode wires 406 and 408 and electrodes 406', 408' is forced to pass through porous strip 412, through adjacent tissue to get around the inner barrier (not shown) and insulative portion 413, and through porous strip 414, to travel from cavity 431" to cavity 433" and vice versa. Thus, electroporation (reversible or irreversible) may take place between tissue adjacent to porous strip 412 and tissue adjacent to porous strip 414. It is further noted that an electric field (V/cm) generated by device 400" may require less voltage than that of device 400. This is because cavities 431" and 433" are adjacent, and thus, porous strips 412 and 414 of device 400" may be closer in proximity than those of device 400. For example, in some embodiments, the dis-tance between porous strips 412 and 414 of device 400" may be about 2 to 3 cm.

Device 400" may be used in a similar manner as device 400 except cavity 622 of inner balloon 620 is filled with a fluid, e.g., air, saline, etc., and cavities 431" and 433" are filled with conductive fluid, e.g., 0.9% saline. Cavities 431" and 433'" may be filled with conductive fluid until porous strips 412 and 414 abut the surrounding tissue.

Figure 3:
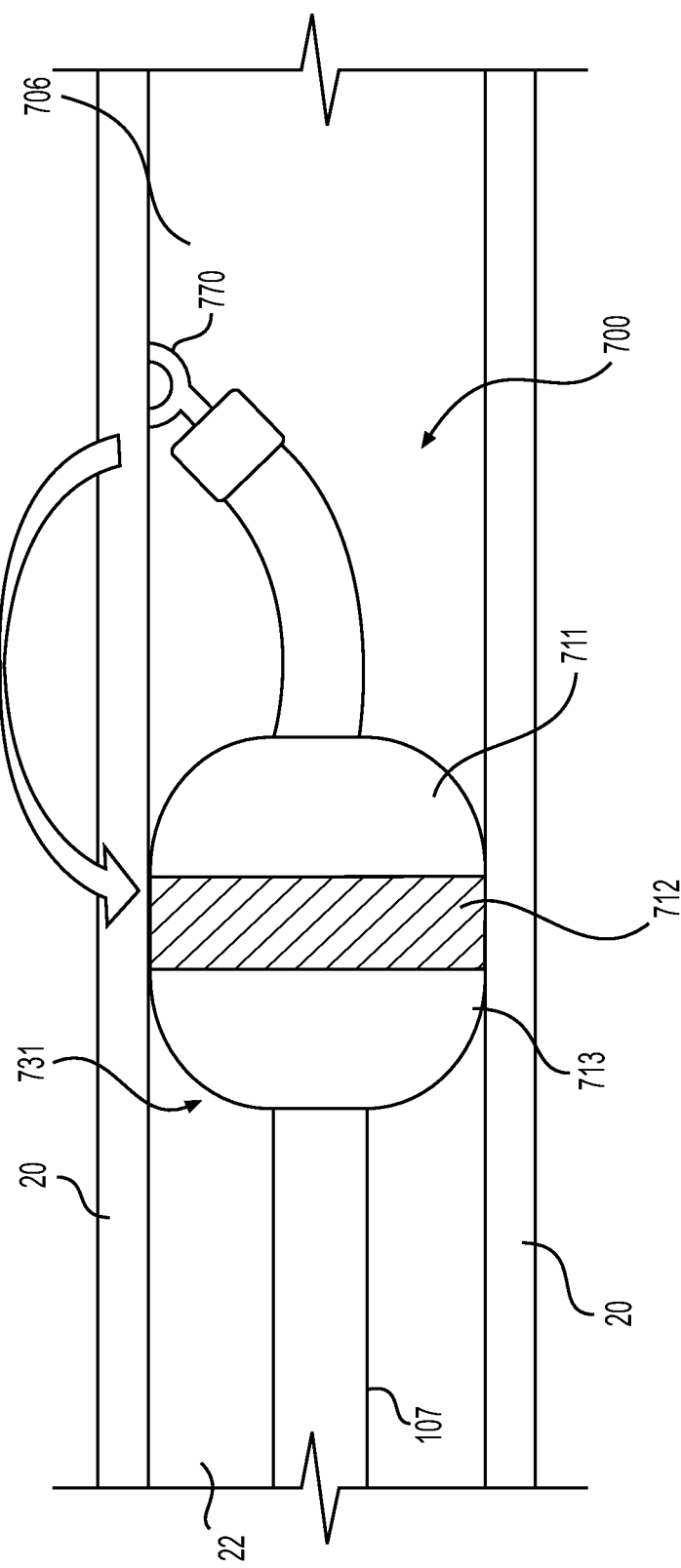
FIG. 3 is a side view of a medical device for electroporation in a body lumen, according to some aspects of the disclosure.

Medical device 700, as shown in FIG. 3, is similar to device 400 in many respects. Similarities and differences between device 400 and device 700 will be described below.

Device 700 may include an electro-spun balloon 731 similar to that of balloon 431 in device 400. Like balloon 431, balloon 731 may house at least one electrode (not shown) and at least one outlet (not shown), configured to dispense conductive fluid. The electrode(s) may be connected to a conductive wire extending through tube 107 to an electrical supply, e.g., a generator (not shown). Furthermore, distal and proximal portions of the membrane of balloons 731 may be coated with an insulating material, e.g., silicone, thereby defining insulated portions 711 and 713. As a result of defining said insulated portions, a circumferential porous strip 712 around balloon 731 may likewise be defined.

However, unlike device 400, device 700 may be without a second balloon. Rather, device 700 may include a steerable distal end 706, and steerable distal end 706 may include a metal, conductive tip 770. Distal end 706 may be articulable/steerable by any suitable means. Metal tip 770 is not particularly limited, and may be, for example, a tip electrode or any suitable biopsy tool. Metal tip 770 may also be a tool configured to deliver drugs or agents, e.g., a needle. Tip 770 may also be connected to another conductive wire extending through tube 107 to an electrical supply, e.g., a generator (not shown). Thus, the electrode(s) within balloon 731 and tip 770 may be oppositely charged, via said electrical supply and their respective conductive wires.

By steering distal end 706 so that metal tip 770 contacts surrounding tissue 20, a generated electric field is forced to pass through porous strip 712, and through adjacent tissue to get around insulative portion 711, to travel from balloon 731 to metal tip 770 and vice versa. Thus, electroporation (reversible or irreversible) may take place between tissue adjacent to porous strip 712 and tissue in contact with metal tip 770. Because metal tip 770 may be in contact with only one side of surrounding tissue 20, device 700 may provide a more targeted electroporation treatment compared to the above-described exemplary devices.

Device 700 may be used in a similar manner as device 400 except only one balloon 731 is filled with conductive fluid, e.g., saline, etc., and distal end 706 is steered so that metal tip 770 may contact one side of surrounding tissue 20.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
a tube;
a first electrode and a second electrode; and
a structure at a distal portion of the tube, wherein the structure defines a first section radially surrounded by a first wall of the structure and a second section radially surrounded by a second wall of the structure, and wherein the structure includes:
an insulative central barrier separating the first section from the second section, an insulative proximal barrier, and
an insulative distal barrier,
wherein a space between the central barrier and the distal barrier defines the first section, and a space between the central barrier and the proximal barrier defines the second section,
wherein the proximal barrier, the central barrier, and the distal barrier are each balloons configured to be inflated;
wherein the first and second sections are configured to be filled with a conductive medium, and
wherein the first electrode is contained within the first section, and the second electrode is contained within the second section.

2. The medical device of claim 1, wherein the first wall and the second wall are porous.

3. The medical device of claim 1, wherein the conductive medium is a fluid.

4. The medical device of claim 1, wherein the conductive medium of the first section is oppositely charged from the conductive medium of the second section, or the conductive medium of the first section is of a different voltage potential than the conductive medium of the second section.

5. The medical device of claim 1, wherein a proximal end of a conductor extended through the tube is connected to an electrical source, and the conductor is configured to supply a current from the electrical source to the first electrode and the second electrode.

6. A medical device, comprising:
a tube;
a first electrode; and
an inflatable structure at a distal portion of the tube, the structure including:
a proximal non-porous barrier,
a central non-porous barrier,
a distal non-porous barrier,
a proximal porous wall connected to the proximal non-porous barrier and the central non-porous barrier, and
a distal porous wall connected to the central non-porous barrier and the distal non-porous barrier;
wherein the proximal porous wall radially surrounds a first cavity configured to be filled with a conductive medium, and
wherein the first electrode is positioned within the first cavity.

7. The medical device of claim 6, wherein the proximal, central, and distal non-porous barriers are insulative.

8. The medical device of claim 6, wherein the proximal non-porous barrier is a first balloon, the central non-porous barrier is a second balloon, and the distal non-porous barrier is a third balloon.

9. The medical device of claim 6, wherein:
the central non-porous barrier is a balloon, and
each of the proximal porous wall and the distal porous wall are connected to the central barrier.

10. The medical device of claim 1, wherein at least one of the first wall or the second wall is porous.

* * * * *